US010905373B2

(12) United States Patent
Lu et al.

(10) Patent No.: US 10,905,373 B2
(45) Date of Patent: Feb. 2, 2021

(54) BREATHING MANAGEMENT MECHANISM

(71) Applicant: Intel Corporation, Santa Clara, CA (US)

(72) Inventors: Mei Lu, Portland, OR (US); Barrett Kenney, Hillsboro, OR (US); Jason Janavicius, Laguna Niguel, CA (US); Saurabh Dadu, Tigard, OR (US); David P. Kuhns, Salem, OR (US); Paul F. Sorenson, Hillsboro, OR (US)

(73) Assignee: Intel Corporation, Santa Clara, CA (US)

( * ) Notice: Subject to any disclaimer, the term of this patent is extended or adjusted under 35 U.S.C. 154(b) by 1003 days.

(21) Appl. No.: 14/864,640

(22) Filed: Sep. 24, 2015

(65) Prior Publication Data

US 2017/0086730 A1 Mar. 30, 2017

(51) Int. Cl.
*A61B 5/00* (2006.01)
*A61B 5/0205* (2006.01)
*A61B 5/08* (2006.01)
*A61B 5/11* (2006.01)
*A61B 5/024* (2006.01)

(52) U.S. Cl.
CPC ............ *A61B 5/486* (2013.01); *A61B 5/0205* (2013.01); *A61B 5/0816* (2013.01); *A61B 5/112* (2013.01); *A61B 5/6829* (2013.01); *A61B 5/7246* (2013.01); *A61B 5/7405* (2013.01); *A61B 5/02438* (2013.01); *A61B 2503/10* (2013.01); *A61B 2562/0219* (2013.01)

(58) Field of Classification Search
CPC ...................................................... A61B 5/486
USPC ........................................................ 434/247
See application file for complete search history.

(56) References Cited

U.S. PATENT DOCUMENTS

| 2010/0324427 | A1 | 12/2010 | Devot et al. |
| 2011/0066041 | A1 | 3/2011 | Pandia et al. |
| 2011/0125044 | A1 | 5/2011 | Rhee et al. |
| 2013/0211482 | A1* | 8/2013 | Piipponen ............ A61N 5/1049 607/100 |
| 2014/0228657 | A1 | 8/2014 | Palley et al. |
| 2015/0073232 | A1 | 3/2015 | Ahmad et al. |

OTHER PUBLICATIONS

PCT Application No. PCT/US2016/042656, Notification Concerning Transmittal of International of International Preliminary Report on Patentability, dated Apr. 5, 2018, 7 pgs.
PCT Search Report and Written Opinion, PCT/US2016/042656, dated Nov. 1, 2016, 16 pages.

* cited by examiner

*Primary Examiner* — Kesha Frisby
(74) *Attorney, Agent, or Firm* — Hanley, Flight and Zimmerman, LLC (57) ABSTRACT

A method is described to facilitate breathing management. The method includes receiving sensory data from one or more wearable devices, recording a breathing pattern of a wearer of the one or more wearable devices based on data received from the sensor array, calculating a body movement of the wearer based on the data received from the sensor array and correlating a wearer breathing pattern with the wearer body movement and heart rate.

25 Claims, 5 Drawing Sheets

BREATHING MANAGEMENT MECHANISM

FIELD

Embodiments described herein generally relate to wearable computing. More particularly, embodiments relate to sports training based wearable devices.

BACKGROUND

Breathing management, important for effective training for various endurance sports, is often neglected by athletes. Moreover, for sports like yoga and meditation, breathing is also an inherent part of the exercise or activity. An optimal pattern and rhythm of deep breathing can assist an athlete to not only draw more oxygen, but also quickly remove carbon dioxide, thus generating energy more efficiently for the activity. Further, during endurance sports training athletes often adhere to workout plans that require near maximum physical exertion for a short period of time, and a recovery time with a period of minimum effort. This cycle is then repeated a number of times (e.g., intervals).

During maximum effort, the training may lead to acute physiological changes and very high heart rates. Thus, it is important for an athlete to recover sufficiently during rest periods before starting the next maximum exertion period, to ensure that heart rate recovers to a lower zone. However, athletes often encounter a situation in which heart rate cannot quickly decrease after maximum effort. Continued training with an elevated heart rate may potentially lead to cardiovascular fatigue and negatively impact long term training effectiveness.

Modern clothing and other wearable accessories may incorporate computing or other advanced electronic technologies. Such computing and/or advanced electronic technologies may be incorporated for various functional reasons or may be incorporated for purely aesthetic reasons. Such clothing and other wearable accessories are generally referred to as "wearable technology" or "wearable computing devices."

Wearable devices are becoming prevalent for enabling users to accomplish various tasks while on the go. For instance, health and fitness, tracking and simple phone-like applications are becoming pervasive. Currently, wearable devices that provide notification based feedback are available. However, applications for these devices are limited.

BRIEF DESCRIPTION OF THE DRAWINGS

Embodiments are illustrated by way of example, and not by way of limitation, in the figures of the accompanying drawings in which like reference numerals refer to similar elements.

DETAILED DESCRIPTION

Embodiments may be embodied in systems, apparatuses, and methods for breathing management, as described below. In the description, numerous specific details, such as component and system configurations, may be set forth in order to provide a more thorough understanding of the present invention. In other instances, well-known structures, circuits, and the like have not been shown in detail, to avoid unnecessarily obscuring the present invention.

Embodiments provide for a breathing management mechanism to lower user heart rate at an appropriate time by analyzing user breathing and heart rate pattern during a workout, and providing audio feedback to the user, such as a reminder or coaching, upon detecting the user is experiencing an elevated heart rate and/or irregular breathing. As a result, the user can use effective breathing to ensure heart rate recovery and restore homeostasis, and prevent cardiovascular fatigue during training.

In a further embodiment, the breathing management mechanism assists in achieving an optimal breathing during a user workout by coordinating body movement. For instance, sensors on one or more wearable devices may detect a user's stride rate while running to determine whether the user's foot is landing. Based on sensor data the breathing management mechanism may provide instruction on breathing strategies to achieve certain breathing patterns. In addition to improving training effectiveness, the instruction may also assist in preventing the user from always landing on the same foot during an exhale, which can potentially lead to long-term injuries.

In yet a further embodiment, the breathing management mechanism may record and analyze a user's breathing pattern (e.g., whether a user is inhaling, exhaling or panting), together with other data (e.g., heart rate, speed, cadence, or body movement). This data enables a user to be aware of breathing patterns during a workout, and assist in developing an optimal breathing strategy that can lead to the most effective training. Additionally, such analyses may help to identify an optimal breathing pattern for the user based on their performance data.

Figure 1:
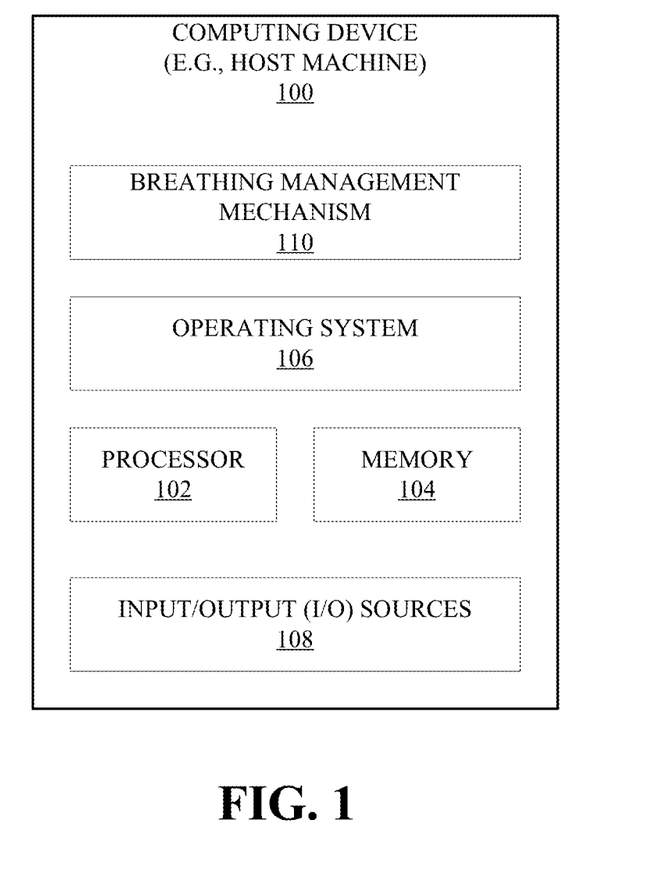
FIG. 1 illustrates a breathing management mechanism at a computing device according to one embodiment.

FIG. 1 illustrates one embodiment of a breathing management mechanism 110 at a computing device 100. In one embodiment, computing device 100 serves as a host machine for hosting breathing management mechanism ("breathing mechanism") 110 that includes a combination of any number and type of components for detecting stimuli and breathing at computing devices, such as computing device 100. In one embodiment, computing device 100 includes a wearable device. Thus, implementation of breathing mechanism 110 results in computing device 100 being an assistive device to provide effective breathing recommendations to a wearer of computing device 100.

In other embodiments, breathing management operations may be performed at a computing device 100 including large computing systems, such as mobile computing devices, such as cellular phones including smartphones, personal digital assistants (PDAs), tablet computers, laptop computers (e.g., notebook, netbook, Ultrabook™, etc.), e-readers, etc. In yet other embodiments, computing device 100 may include server computers, desktop computers, etc., and may further include set-top boxes (e.g., Internet-based cable television set-top boxes, etc.), global positioning system (GPS)-based devices, etc.

Computing device 100 may include an operating system (OS) 106 serving as an interface between hardware and/or physical resources of the computer device 100 and a user. Computing device 100 further includes one or more processors 102, memory devices 104, network devices, drivers, or the like, as well as input/output (I/O) sources 108, such as touchscreens, touch panels, touch pads, virtual or regular keyboards, virtual or regular mice, etc.

Throughout this document, terms like "logic", "component", "module", "framework", "engine", "point", and the like, may be referenced interchangeably and include, by way of example, software, hardware, and/or any combination of software and hardware, such as firmware. Further, any use of a particular brand, word, term, phrase, name, and/or acronym, such as "avatar", "avatar scale factor", "scaling", "animation", "human face", "facial feature points", "zooming-in", "zooming-out", etc., should not be read to limit embodiments to software or devices that carry that label in products or in literature external to this document.

It is contemplated that any number and type of components may be added to and/or removed from breathing mechanism 110 to facilitate various embodiments including adding, removing, and/or enhancing certain features. For brevity, clarity, and ease of understanding of breathing mechanism 110, many of the standard and/or known components, such as those of a computing device, are not shown or discussed here. It is contemplated that embodiments, as described herein, are not limited to any particular technology, topology, system, architecture, and/or standard and are dynamic enough to adopt and adapt to any future changes.

Figure 2:
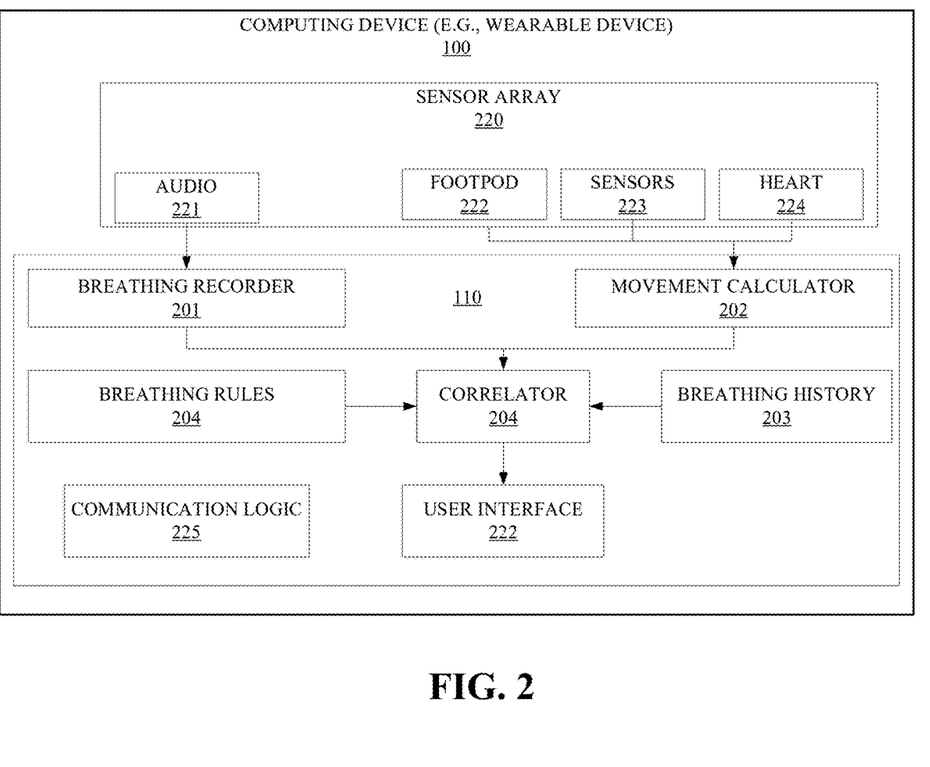
FIG. 2 illustrates one embodiment of a breathing management mechanism.

FIG. 2 illustrates a breathing management mechanism 110 employed at computing device 100. In one embodiment, breathing management mechanism 110 may include any number and type of components, such as: breathing recorder 201, movement calculator 202, breathing history module 203, breathing rules module 204 and correlator 205.

In one embodiment, breathing recorder 201 records a breathing pattern of a wearer (or user) of computing device 100 via a sensor array 220. In such an embodiment, breathing recorder 201 receives audio signals from an audio sensor 221 included in sensor array 220. Exemplary audio sensors 221 include a bone conduction microphone in the nose bridge of sunglasses and an acoustic microphone close to user's mouth such as in the frame of the glasses.

According to one embodiment, movement calculator 202 receives data from sensor array 220 and calculates a stride pattern and/or body movement of a computing device 100 wearer. In such an embodiment, movement calculator 202 may receive data regarding steps from an inertial footpod 222 included in sensor array 220 in order to track foot step measurements (e.g., speed, distance travelled, pace, etc.).

Further, body movement may be calculated in response to receiving data from sensors 223. According to one embodiment, sensors 223 include one or more of an accelerator, gyroscope and compass to assist in movement calculations. In a further embodiment, movement calculator 202 may receive data from a heart rate monitor 224 included in sensor array 220 in order to record a user's heart rate. Sensor array 220 may also include an image capturing device, such as a camera. Such a device may include various components, such as an optics assembly, an image sensor, an image/video encoder, etc.

In a further embodiment, sensor array 220 may include other types of sensing components, such as context-aware sensors (e.g., myoelectric sensors, temperature sensors, facial expression and feature measurement sensors working with one or more cameras, environment sensors (such as to sense background colors, lights, etc.), biometric sensors (such as to detect fingerprints, facial points or features, etc.), and the like.

Figure 3:
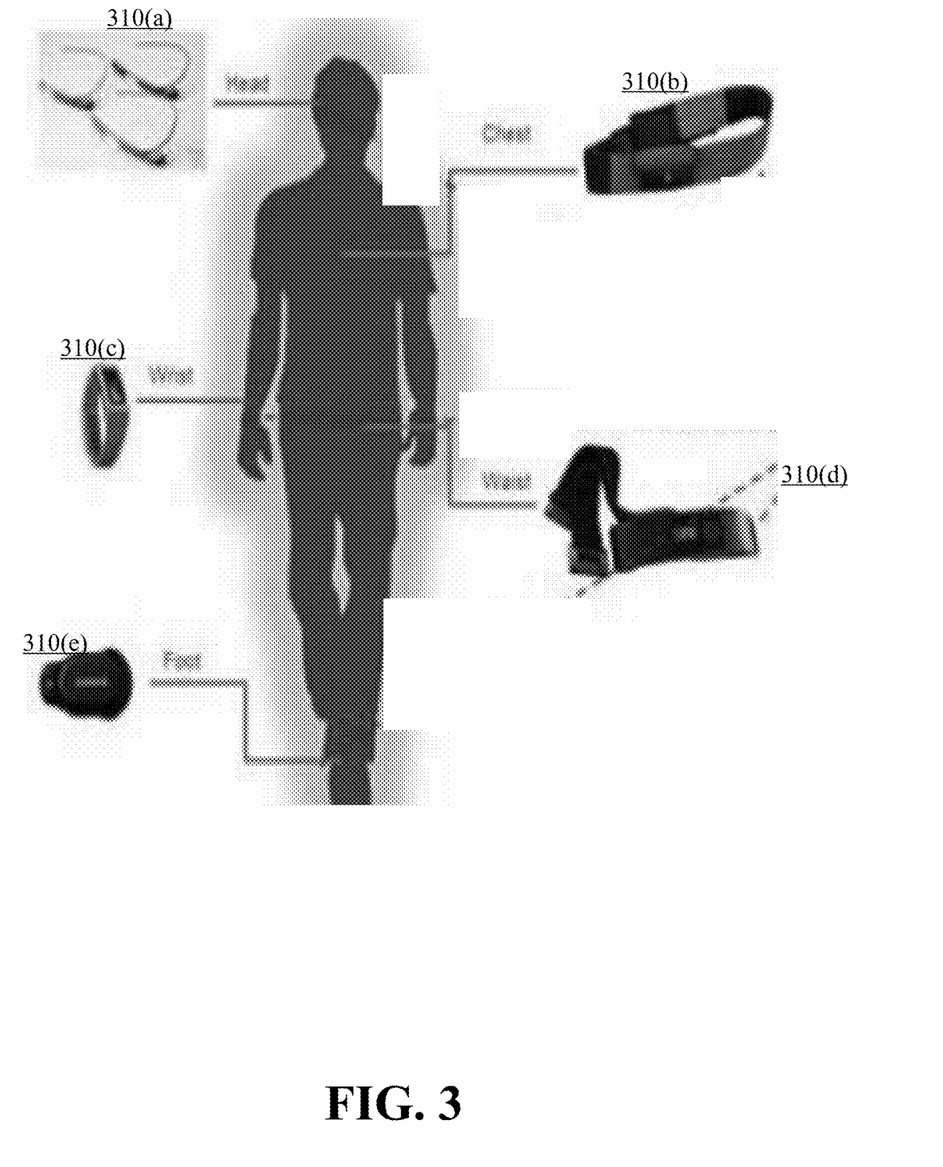
FIG. 3 illustrates one embodiment of wearable devices implemented by a breathing management mechanism.

According to one embodiment sensors in sensor array may be included in multiple wearable devices and transmit data (raw or analyzed) data to breathing management mechanism 110. As discussed above, data may include heart rate, steps taken, real time video (such as from a head worn wearable device), etc. FIG. 3 illustrates one embodiment of wearable devices from which breathing management mechanism 110 may receive data. As shown in FIG. 3, devices 310(a)-310(e) may be worn on a user's head, chest, wrist, waist and foot, respectively. In such embodiments, data is transmitted from each device 310 to context sensing engine 202.

According to one embodiment, breathing management mechanism 110 may be located at any of the wearable devices 310. In such an embodiment, breathing management mechanism 110 (e.g., as implemented in a wearable device such as device 310(a)) may be in communication with the other wearable devices over one or more networks (e.g., Body Area Network (BAN), cloud network, the Internet, intranet, cellular network, proximity or near proximity networks, etc.).

Referring back to FIG. 2, correlator 204 provides context detection based on a user's breathing and heart rate patterns to determine whether a reminder/advice/or audio tone playback for deep breathing is needed. In one embodiment, correlator 204 receives breathing pattern data from breathing recorder 201, as well as body movement, stride pattern and heart rata data from movement calculator 202, in order to correlate a breathing pattern with stride rate/body movement and heart rate.

According to one embodiment, correlator 204 may also provide correlation based upon the user's breathing pattern history. In such an embodiment, breathing history module 203 provides a user's breathing pattern and workout history to correlator 204. In a further embodiment, breathing rules module 204 provides breathing rules to correlator 204 that are to be applied to the correlation calculation.

User interface 222 provides for user interaction with computing device 100. In one embodiment, user interface 222 provides feedback to the user regarding a breathing pattern. In such an embodiment, an audio reminder advises a user to take deep breaths when needed. Further, coaching feedback or auditory input may guide a user toward a desired breathing pattern during a training or workout. In a further embodiment, user interface 222 enables a user to interact via gestures and/or audio commands in order to access breathing mechanism 110.

Communication logic 225 may be used to facilitate dynamic communication and compatibility between with various other computing devices (such as a mobile computing device, a desktop computer, a server computing device, etc.), storage devices, databases and/or data sources, such as database 240, networks (e.g., cloud network, the Internet, intranet, cellular network, proximity networks, such as Bluetooth, Bluetooth low energy (BLE), Bluetooth Smart, Wi-Fi proximity, Radio Frequency Identification (RFID), Near Field Communication (NFC), Body Area Network (BAN), etc.), connectivity and location management techniques, software applications/websites), programming languages, etc., while ensuring compatibility with changing technologies, parameters, protocols, standards, etc.

It is contemplated that any number and type of components 201-205 of breathing mechanism 110 may not necessarily be at a single computing device and may be allocated among or distributed between any number and type of computing devices having (but are not limited to) server computing devices, cameras, PDAs, mobile phones (e.g., smartphones, tablet computers, etc.), personal computing devices (e.g., desktop devices, laptop computers, etc.), smart televisions, servers, wearable devices, media players, any smart computing devices, and so forth. Further examples include microprocessors, graphics processors or engines, microcontrollers, application specific integrated circuits (ASICs), and so forth. Embodiments, however, are not limited to these examples.

Figure 4:
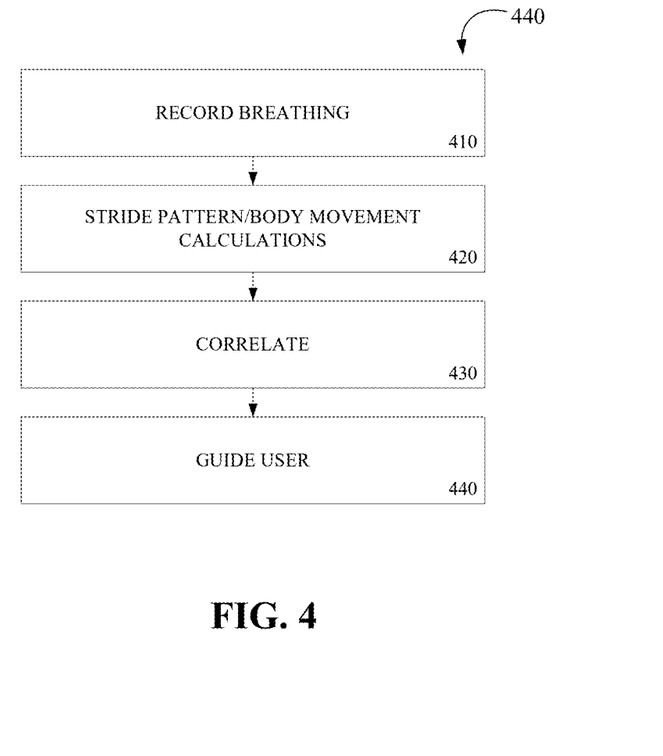
FIG. 4 is a flow diagram illustrating one embodiment of a process performed by a breathing management mechanism.

FIG. 4 is a flow diagram illustrating one embodiment of a process 400 performed by a breathing management mechanism. Process 400 may be performed by processing logic that may comprise hardware (e.g., circuitry, dedicated logic, programmable logic, etc.), software (such as instructions run on a processing device), or a combination thereof. In one embodiment, method 400 may be performed by breathing management mechanism 110. The processes of method 400 are illustrated in linear sequences for brevity and clarity in presentation; however, it is contemplated that any number of them can be performed in parallel, asynchronously, or in different orders. For brevity, clarity, and ease of understanding, many of the details discussed with reference to FIGS. 1-3 may not be discussed or repeated here.

At processing block 410, a breathing pattern is recorded by breathing recorder 201. At processing block 420, stride pattern and body movement are calculated at movement calculator 202. At processing block 430, correlates a breathing pattern with the calculated stride rate/body movement and heart rate, as discussed above. At processing block 440, the user is guided via user interface 222 regarding a breathing pattern.

As discussed above athletic activity stresses physiological systems. For example, interval training is a method widely adopted by endurance athletes for sports training. During these interval sessions an athlete will endure cycles of a high intensity period followed by a recovery period. During the high intensity periods, the athlete often exerts maximum effort. An athlete often exerts near maximum effort to bring heart rate to very high zones, for example, tempo (84-94% of maximum heart rate), lactate threshold (95-105% of maximum heart rate), VO2 Max zone (106%-120% of maximum heart rate) and anaerobic threshold (>120% of maximum heart rate).

The effort results in acute increases or decreases to physiological systems, including a depletion of anaerobic energy stores, a decrease in muscle oxygenation, an increase in breathing rate, as well as other changes. The athlete can only sustain these high intensities for a given period of time. Moreover, intensity level relative to individual ability is inversely correlated with the length of time a given intensity can be sustained. At the completion of these high intensity intervals athletes may wish to return to or toward homeostatic states, for example, achieving a reduced heart rate to a specific level (e.g., <68% of the maximum heart rate). However, athletes often encounter challenges to lower their heat rate and restore homeostasis. The more fatigued, the harder it is to recover heart rate.

Thus, the above described breathing management mechanism 110 may be implemented to overcome such challenges for lowering the heart rate via effective breathing. In one embodiment, breathing management mechanism 110 guides a user to effective recovery after an intense training interval. In such an embodiment, correlator 204 tracks and analyzes a user's heart rate patterns from historical workouts to come up with an understanding of a user's healthy/typical recovery time from tempo zones, lactate threshold, VO2 Max or anaerobic threshold. The healthy (or typical) recovery time may be calculated from historical workouts received from breathing history module 203 and be effective during active training periods for an individual.

For example, a tempo zone typical recovery time is the average recovery time of the first one or two tempo intervals during each workout. During a workout, correlator 204 may track a user's heart rate pattern in real time to determine whether a recovery time is 50% longer than a healthy/typical recovery time. Further, breathing recorder 201 analyzes a user's breathing noise to determine whether the user is panting (e.g., when a user is taking heavy and short breath). When both of the above conditions are true, user interface 222 may play an audio reminder, such as "Please take deep breath to lower your heart rate," or playback designed audio tones that can guide the user toward deep breathing.

In another embodiment, breathing management mechanism 110 may guide a user toward an optimal breathing pattern. In this embodiment, movement calculator 202 analyzes a user's movement (e.g., stride rate and foot movement) while running, and provide inhale or exhale advice so that breathing is coordinated with movement. For initial advice, a user can be guided toward 3:2 (three strides per inhale and two strides per exhale) pattern for easy workout and 2:1 for hard workout. Further, a user may be guided to avoid always landing on the same foot while exhaling. Additionally, a user may adjust the patterns and try for a pattern that works best for the individual.

In yet another embodiment, breathing management mechanism 110 breathing patterns of inhaling, exhaling or panting are recorded together with other data e.g., time, distance, speed, heart rate, stride rate and body movement) throughout the workout. After the workout, a user can view the data along a timeline via user interface 222 to learn points at which there is panting, and how inhaling or exhaling is coordinated with stride or body movement. The analytics of historical data may help to identify the optimal breathing patterns. Further, breathing management mechanism 110 may be implemented during training or a race to provide advice to tune a user to the best patterns. Additionally, breathing management mechanism 110 may also be used for Yoga where appropriate breathing instructions may be provided according to the user's body movement.

Figure 5:
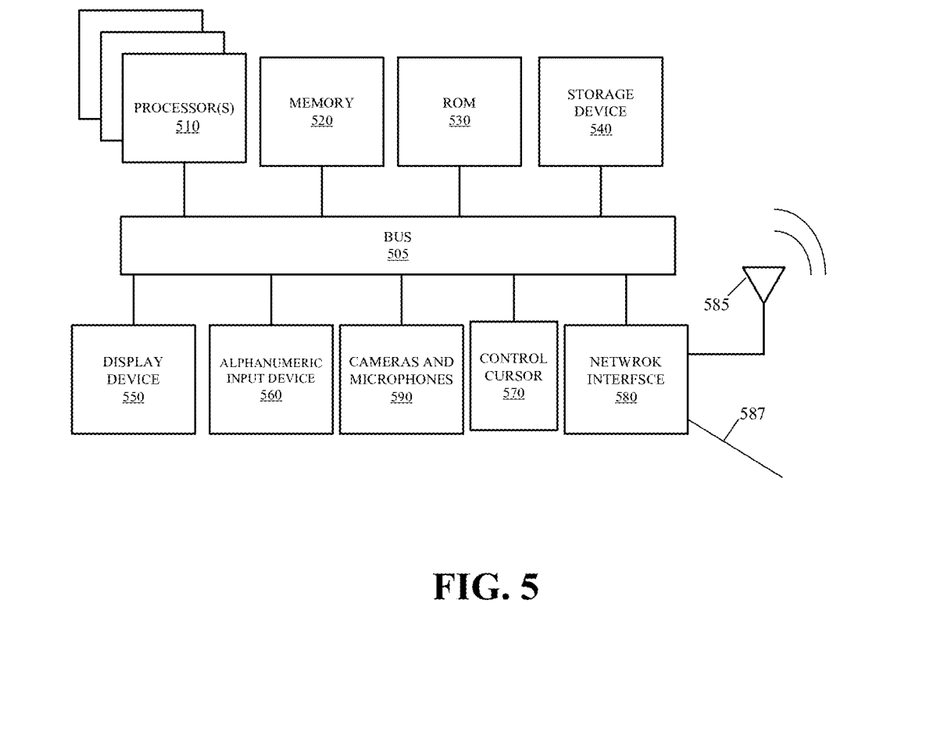
FIG. 5 illustrates a computer system suitable for implementing embodiments of the present disclosure.

FIG. 5 illustrates a computer system suitable for implementing embodiments of the present disclosure. Computing system 500 includes bus 505 (or, for example, a link, an interconnect, or another type of communication device or interface to communicate information) and processor 510 coupled to bus 505 that may process information. While computing system 500 is illustrated with a single processor, electronic system 500 and may include multiple processors and/or co-processors, such as one or more of central processors, graphics processors, and physics processors, etc. Computing system 500 may further include random access memory (RAM) or other dynamic storage device 520 (referred to as main memory), coupled to bus 505 and may store information and instructions that may be executed by processor 510. Main memory 520 may also be used to store temporary variables or other intermediate information during execution of instructions by processor 510.

Computing system 500 may also include read only memory (ROM) and/or other storage device 530 coupled to bus 505 that may store static information and instructions for processor 510. Date storage device 540 may be coupled to bus 505 to store information and instructions. Date storage device 540, such as magnetic disk or optical disc and corresponding drive may be coupled to computing system 500.

Computing system 500 may also be coupled via bus 505 to display device 550, such as a cathode ray tube (CRT), liquid crystal display (LCD) or Organic Light Emitting Diode (OLED) array, to display information to a user. User input device 560, including alphanumeric and other keys, may be coupled to bus 505 to communicate information and command selections to processor 510. Another type of user input device 560 is cursor control 570, such as a mouse, a trackball, a touchscreen, a touchpad, or cursor direction keys to communicate direction information and command selections to processor 510 and to control cursor movement on display 550. Camera and microphone arrays 590 of computer system 500 may be coupled to bus 505 to observe gestures, record audio and video and to receive and transmit visual and audio commands.

Computing system 500 may further include network interface(s) 580 to provide access to a network, such as a local area network (LAN), a wide area network (WAN), a metropolitan area network (MAN), a personal area network (PAN), Bluetooth, a cloud network, a mobile network (e.g., $3^{rd}$ Generation (3G), etc.), an intranet, the Internet, etc. Network interface(s) 580 may include, for example, a wireless network interface having antenna 585, which may represent one or more antenna(e). Network interface(s) 580 may also include, for example, a wired network interface to communicate with remote devices via network cable 587, which may be, for example, an Ethernet cable, a coaxial cable, a fiber optic cable, a serial cable, or a parallel cable.

Network interface(s) 580 may provide access to a LAN, for example, by conforming to IEEE 802.11b and/or IEEE 802.11g standards, and/or the wireless network interface may provide access to a personal area network, for example, by conforming to Bluetooth standards. Other wireless network interfaces and/or protocols, including previous and subsequent versions of the standards, may also be supported.

In addition to, or instead of, communication via the wireless LAN standards, network interface(s) 580 may provide wireless communication using, for example, Time Division, Multiple Access (TDMA) protocols, Global Systems for Mobile Communications (GSM) protocols, Code Division, Multiple Access (CDMA) protocols, and/or any other type of wireless communications protocols.

Network interface(s) 580 may include one or more communication interfaces, such as a modem, a network interface card, or other well-known interface devices, such as those used for coupling to the Ethernet, token ring, or other types of physical wired or wireless attachments for purposes of providing a communication link to support a LAN or a WAN, for example. In this manner, the computer system may also be coupled to a number of peripheral devices, clients, control surfaces, consoles, or servers via a conventional network infrastructure, including an Intranet or the Internet, for example.

It is to be appreciated that a lesser or more equipped system than the example described above may be preferred for certain implementations. Therefore, the configuration of computing system 500 may vary from implementation to implementation depending upon numerous factors, such as price constraints, performance requirements, technological improvements, or other circumstances. Examples of the electronic device or computer system 500 may include without limitation a mobile device, a personal digital assistant, a mobile computing device, a smartphone, a cellular telephone, a handset, a one-way pager, a two-way pager, a messaging device, a computer, a personal computer (PC), a desktop computer, a laptop computer, a notebook computer, a handheld computer, a tablet computer, a server, a server array or server farm, a web server, a network server, an Internet server, a work station, a mini-computer, a main frame computer, a supercomputer, a network appliance, a web appliance, a distributed computing system, multiprocessor systems, processor-based systems, consumer electronics, programmable consumer electronics, television, digital television, set top box, wireless access point, base station, subscriber station, mobile subscriber center, radio network controller, router, hub, gateway, bridge, switch, machine, or combinations thereof.

Embodiments may be implemented as any or a combination of: one or more microchips or integrated circuits interconnected using a parent board, hardwired logic, software stored by a memory device and executed by a microprocessor, firmware, an application specific integrated circuit (ASIC), and/or a field programmable gate array (FPGA). The term "logic" may include, by way of example, software or hardware and/or combinations of software and hardware.

Embodiments may be provided, for example, as a computer program product which may include one or more machine-readable (or computer-readable) media having stored thereon machine-executable instructions that, when executed by one or more machines such as a computer, network of computers, or other electronic devices, may result in the one or more machines carrying out operations in accordance with embodiments described herein. A machine-readable medium may include, but is not limited to, floppy diskettes, optical disks, CD-ROMs (Compact Disc-Read Only Memories), and magneto-optical disks, ROMs, RAMs, EPROMs (Erasable Programmable Read Only Memories), EEPROMs (Electrically Erasable Programmable Read Only Memories), magnetic or optical cards, flash memory, or other type of media/machine-readable medium suitable for storing machine-executable instructions.

Moreover, embodiments may be downloaded as a computer program product, wherein the program may be transferred from a remote computer (e.g., a server) to a requesting computer (e.g., a client) by way of one or more data signals embodied in and/or modulated by a carrier wave or other propagation medium via a communication link (e.g., a modem and/or network connection).

References to "one embodiment", "an embodiment", "example embodiment", "various embodiments", etc., indicate that the embodiment(s) so described may include particular features, structures, or characteristics, but not every embodiment necessarily includes the particular features, structures, or characteristics. Further, some embodiments may have some, all, or none of the features described for other embodiments.

In the following description and claims, the term "coupled" along with its derivatives, may be used. "Coupled" is used to indicate that two or more elements co-operate or interact with each other, but they may or may not have intervening physical or electrical components between them.

As used in the claims, unless otherwise specified the use of the ordinal adjectives "first", "second", "third", etc., to describe a common element, merely indicate that different instances of like elements are being referred to, and are not intended to imply that the elements so described must be in a given sequence, either temporally, spatially, in ranking, or in any other manner.

The following clauses and/or examples pertain to further embodiments or examples. Specifics in the examples may be used anywhere in one or more embodiments. The various features of the different embodiments or examples may be variously combined with some features included and others excluded to suit a variety of different applications. Examples may include subject matter such as a method, means for performing acts of the method, at least one machine-readable medium including instructions that, when performed by a machine cause the machine to performs acts of the method, or of an apparatus or system for facilitating hybrid communication according to embodiments and examples described herein.

Some embodiments pertain to Example 1 that includes one or more wearable devices having an array of sensors, a breathing recorder to record a breathing pattern of a wearer of the one or more wearable devices based on data received from the sensor array, a movement calculator to calculate a body movement of the wearer based on data received from the sensor array and correlator to correlate a wearer breathing pattern with the wearer body movement.

Example 2 includes the subject matter of Example 1, further comprising a breathing history module to provide data regarding a breathing pattern and workout history for the wearer.

Example 3 includes the subject matter of Example 2, wherein the correlator correlates the wearer breathing pattern with the wearer body movement and heart rate, based on the breathing pattern and workout history.

Example 4 includes the subject matter of Example 1, further comprising a breathing rules module to provide breathing rules to the correlator that are to be applied to the correlation.

Example 5 includes the subject matter of Example 1, further comprising a user interface to provide feedback to the wearer regarding a breathing pattern.

Example 6 includes the subject matter of Example 5, wherein the user interface provides an audio reminder to advise the wearer to take needed breaths.

Example 8 includes the subject matter of Example 1, wherein the breathing recorder receives audio signals from an audio sensor included in the sensor array.

Example 9 includes the subject matter of Example 8, wherein the audio sensor comprises one of a bone conduction microphone and an acoustic microphone.

Example 10 includes the subject matter of Example 1, wherein the movement calculator calculates movement based on data received from one or more of an accelerator, gyroscope and compass to assist in movement calculations.

Example 11 includes the subject matter of Example 10, wherein the movement calculator calculates a stride pattern of the wearer.

Example 12 includes the subject matter of Example 11, wherein the correlator correlates the wearer breathing pattern with the wearer stride pattern.

Example 13 includes the subject matter of Example 11, wherein the movement calculator receives data from an inertial footpod included in the sensor array to track foot step measurements.

Example 14 includes the subject matter of Example 10, wherein the movement calculator calculates a heart rate of the wearer based on data from a heart rate monitor included in the sensor array.

Some embodiments pertain to Example 15 that includes a method to facilitate breathing management comprising receiving sensory data from a sensor array implemented at one or more wearable devices, recording a breathing pattern of a wearer of the one or more wearable devices based on data received from the sensor array, calculating a body movement of the wearer based on the data received from the sensor array and correlating a wearer breathing pattern with the wearer body movement.

Example 16 includes the subject matter of Example 15, further comprising receiving data from a breathing history module regarding a breathing pattern and workout history for the wearer.

Example 17 includes the subject matter of Example 15, further comprising receiving breathing rules from a breathing rules module that are to be applied to the correlation.

Example 18 includes the subject matter of Example 15, further comprising providing an audio reminder via a user interface to advise the wearer to take needed breaths.

Example 19 includes the subject matter of Example 18, further comprising providing auditory coaching feedback to guide the wearer towards a desired breathing pattern during a training session.

Example 20 includes the subject matter of Example 15, further comprising calculating a stride pattern of the wearer.

Example 21 includes the subject matter of Example 20, wherein the correlator correlates the wearer breathing pattern with the wearer stride pattern and heart rate.

Some embodiments pertain to Example 22 that includes at least one machine-readable medium comprising a plurality of instructions that in response to being executed on a computing device, causes the computing device to carry out operations comprising receiving sensory data from a sensor array implemented at one or more wearable devices, recording a breathing pattern of a wearer of the one or more wearable devices based on data received from the sensor array, calculating a body movement of the wearer based on the data received from the sensor array and correlating a wearer breathing pattern with the wearer body movement and heart rate.

Example 23 includes the subject matter of Example 22, comprising a plurality of instructions that in response to being executed on a computing device, causes the computing device to further carry out operations comprising receiving data from a breathing history module regarding a breathing pattern and workout history for the wearer.

Example 24 includes the subject matter of Example 23, comprising a plurality of instructions that in response to being executed on a computing device, causes the computing device to further carry out operations comprising receiving breathing rules from a breathing rules module that are to be applied to the correlation.

Example 25 includes the subject matter of Example 23, comprising a plurality of instructions that in response to being executed on a computing device, causes the computing device to further carry out operations comprising providing auditory coaching feedback to guide the wearer towards a desired breathing pattern during a training session.

Some embodiments pertain to Example 26 that includes a system to facilitate breathing management comprising a first wearable device, a network coupled to the first wearable device a second wearable device coupled to the network, and a breathing management unit coupled to the network comprising a breathing recorder to record a breathing pattern of a wearer of the one or more wearable devices based on data received from the sensor array, a movement calculator to calculate a body movement of the wearer based on data received from the sensor array; and a correlator to correlate a wearer breathing pattern with the wearer body movement.

Some embodiments pertain to Example 27 that includes a breathing management system comprising means for receiving sensory data from a sensor array implemented at one or more wearable devices, means for recording a breathing pattern of a wearer of the one or more wearable devices based on data received from the sensor array, means for calculating a body movement of the wearer based on the data received from the sensor array and means for correlating a wearer breathing pattern with the wearer body movement and heart rate.

Example 28 includes the subject matter of Example 27, further comprising means for receiving data from a breathing history module regarding a breathing pattern and workout history for the wearer.

Example 29 includes the subject matter of Example 28, further comprising means for receiving breathing rules from a breathing rules module that are to be applied to the correlation.

Example 30 includes the subject matter of Example 28, further comprising means for providing auditory coaching feedback to guide the wearer towards a desired breathing pattern during a training session.

Some embodiments pertain to Example 31 that includes at least one machine-readable medium comprising a plurality of instructions that in response to being executed on a computing device, causes the computing device to carry out the method of claims 15-21.

The drawings and the forgoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions in any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

What is claimed is:

1. An apparatus to facilitate breathing management, the apparatus comprising:
    one or more wearable devices having an array of sensors;
    a breathing recorder to record a first breathing pattern of a wearer of the one or more wearable devices based on data received from the sensor array;
    a movement calculator to calculate a first body movement of the wearer based on the data received from the sensor array;
    a correlator to correlate the first breathing pattern with the first body movement and to analyze heart rate patterns of the wearer from historical workouts to identify a recovery time for the wearer;
    a breathing management mechanism to generate feedback for the wearer to achieve a second breathing pattern that lowers the heart rate via breathing based on the recovery time; and
    a user interface to provide the feedback to the wearer, the feedback to guide the wearer of a second body movement to achieve the second breathing pattern for the first based on the correlated first breathing pattern and first body movement.

2. The apparatus of claim 1, further including a breathing history module to provide data regarding the first breathing pattern and workout history for the wearer.

3. The apparatus of claim 2, wherein the correlator is to correlate the first breathing pattern with the first body movement and heart rate, based on the first breathing pattern and the workout history.

4. The apparatus of claim 1, further including a breathing rules module to provide breathing rules to the correlator that are to be applied to correlation of the first breathing pattern with the first body movement.

5. The apparatus of claim 1, further including the user interface to provide audio feedback to the wearer regarding the second breathing pattern.

6. The apparatus of claim 5, wherein the user interface provide an audio reminder to advise the wearer to take breaths.

7. The apparatus of claim 5, wherein the user interface provide auditory coaching feedback to guide the wearer towards the second breathing pattern during a training session.

8. The apparatus of claim 1, wherein the breathing recorder is to receive audio signals from an audio sensor included in the sensor array.

9. The apparatus of claim 8, wherein the audio sensor includes at least one of a bone conduction microphone or an acoustic microphone.

10. The apparatus of claim 1, wherein the movement calculator is to calculate movement based on data received from one or more of an accelerometer, a gyroscope, or a compass.

11. The apparatus of claim 10, wherein the movement calculator is to calculate a stride pattern of the wearer.

12. The apparatus of claim 11, wherein the correlator is to correlate the first breathing pattern with the stride pattern.

13. The apparatus of claim 11, wherein the movement calculator is to receive data from an inertial footpod included in the sensor array to track footstep measurements.

14. The apparatus of claim 10, wherein the movement calculator is to calculate a heart rate of the wearer based on data from a heart rate monitor included in the sensor array.

15. A method to facilitate breathing management comprising:
    receiving sensory data from a sensor array implemented at one or more wearable devices;
    recording a breathing pattern of a wearer of the one or more wearable devices based on the sensory data;
    calculating a first body movement of the wearer based on the sensory data;
    correlating the first breathing pattern with the first body movement;
    analyzing heart rate patterns of the wearer for historical workouts to identify a recovery time for the wearer;
    generating feedback for the wearer to achieve a second breathing pattern that lowers a heart rate of the wearer via breathing based on the recovery time; and
    providing the feedback to the wearer to guide the wearer of a second body movement to achieve the second breathing pattern based on the correlated first breathing pattern and body movement.

16. The method of claim 15, further including receiving data from a breathing history module regarding the first breathing pattern and a workout history of the wearer.

17. The method of claim 15, further including receiving breathing rules from a breathing rules module that are to be applied to correlation of the first breathing pattern with the first body movement.

18. The method of claim 15, further including providing an audio reminder via a user interface to advise the wearer to take breaths.

19. The method of claim 18, further including providing auditory coaching feedback to guide the wearer towards the second breathing pattern during a training session.

20. The method of claim 15, wherein calculating the first body movement includes calculating a stride pattern of the wearer.

21. The method of claim 20, wherein the correlating of the first pattern with the first body movement includes correlating the first breathing pattern with the wearer stride pattern.

22. At least one non-transitory machine-readable medium comprising instructions that, when executed, cause one or more processors to at least:
    receive sensory data from a sensor array implemented at one or more wearable devices;
    record a first breathing pattern of a wearer of the one or more wearable devices based on the sensory data;
    calculate a first body movement of the wearer based on the sensory data;
    correlate the first breathing pattern with the first body movement and heart rate;
    analyze heart rate patterns of the wearer from historical workouts to identify a recovery time for the wearer;
    generate feedback for the wearer to achieve a second breathing pattern that lowers the heart rate via breathing based on the recovery time; and
    provide the feedback to the wearer to guide the wearer of body movement to achieve the second breathing pattern based on the correlated first breathing pattern and first body movement.

23. The non-transitory machine-readable medium of claim 22, wherein the instructions, when executed, cause the one or more processors to receive data from a breathing history module regarding the first breathing pattern and workout history of the wearer.

24. The non-transitory machine-readable medium of claim 23, wherein the instructions, when executed, cause the one or more processors to receive breathing rules from a breathing rules module that are to be applied to correlation of the first breathing pattern with the first body movement and the heart rate.

25. The non-transitory machine-readable medium of claim 23, wherein the instructions, when executed, cause the one or more processors to provide auditory coaching feedback to guide the wearer towards the second breathing pattern during a training session.

* * * * *